United States Patent [19]

Fujiwara et al.

[11] Patent Number: 5,254,729
[45] Date of Patent: Oct. 19, 1993

[54] METHOD FOR PURIFYING GLYCINE

[75] Inventors: Kenji Fujiwara; Susumu Yoshinaga; Yuji Matsuu; Hiroshi Kato; Atsuhiko Hiai, all of Osaka, Japan

[73] Assignee: Mitsui Toatsu Chemicals, Inc., Tokyo, Japan

[21] Appl. No.: 705,363

[22] Filed: May 24, 1991

[30] Foreign Application Priority Data

May 31, 1990 [JP] Japan .................... 2-140086

[51] Int. Cl.$^5$ .................... C07C 229/08; C07C 215/08
[52] U.S. Cl. .................................... 562/554
[58] Field of Search ........................... 562/554

[56] References Cited

U.S. PATENT DOCUMENTS

| | | | |
|---|---|---|---|
| 3,536,726 | 10/1970 | Fink et al. | 260/295 |
| 3,875,221 | 4/1975 | Mihara et al. | 562/554 |
| 4,299,978 | 11/1981 | Nakayasu et al. | 562/554 |
| 4,619,948 | 10/1986 | Kennedy et al. | 521/52 |

OTHER PUBLICATIONS

Semmens et al., J.-Am. Water Works Assoc., 78(5), pp. 89-93 (1986) (Abstract).
Patent Abstracts of Japan, vol. 11, No. 398, Dec. 25, 1987, 62-158246.
Patent Abstracts of Japan, vol. 10, No. 36, Feb. 13, 1986, 60-188353.
Japanese Patents Report, CH Section, vol. 79, No. 5, Mar. 2, 1979, J7 9001686.

Primary Examiner—José G. Dees
Assistant Examiner—B. Frazier
Attorney, Agent, or Firm—Burns, Doane, Swecker & Mathis

[57] ABSTRACT

A method for purifying glycine characterized by comprising the steps of adjusting the pH of an aqueous glycine solution to 6 or less with a mineral acid and/or an organic acid or an acidic cation exchange resin and subsequently decoloring said aqueous glycine solution by active carbon treatment.

4 Claims, No Drawings

METHOD FOR PURIFYING GLYCINE

BACKGROUND OF THE INVENTION (i) Field of the Invention

The present invention relates to a method for purifying glycine. More specifically, the present invention relates to a method for obtaining substantially colorless glycine from an aqueous glycine solution. Glycine is a useful compound which is widely used as a raw material for food additives of processed foodstuffs, agricultural chemicals and medicines.

(ii) Description of the Prior Art

Heretofore, as methods for preparing glycine, there are known mainly (1) an amination method using monochloroacetic acid, (2) the Strecker method, and (3) the hydantoin method.

(1) In the amination method using monochloroacetic acid, the raw materials are expensive, and an ammonium salt of a mineral acid such as ammonium chloride, iminodiacetic acid and nitrilotriacetic acid are produced, and a complex process is required to separate these products from glycine.

(2) The Strecker method comprises reacting ammonia and glycolonitrile which can be synthesized from hydrocyanic acid and formalin, and then carrying out hydrolysis with an alkali such as sodium hydroxide to form a metal salt of glycine. Thus, it is impossible to directly produce free glycine.

As a technique for preparing free glycine from this metal salt of glycine, there are known (a) a process for ion exchanging the metal salt of glycine with an acidic cation exchange resin and (b) a process for neutralizing the metal salt with a mineral acid such as sulfuric acid to effect desalting. In the case that an ion exchange resin 1 is used, a very large amount of the resin is necessary, and on the other hand, in the case that sulfuric acid is used as a mineral acid, it is difficult to separate, from glycine, sodium sulfate which is a neutral salt and iminodiacetic acid which is one of the by-products, and the treatment of these neutral salts is troublesome.

(3) The hydantoin method comprises reacting glycolonitrile, which can be synthesized from hydrocyanic acid and formaldehyde, with ammonia and a carbon dioxide gas in the presence of water to form hydantoin, and then hydrolyzing the same to prepare glycine. If hydrocyanic acid is replaced with sodium prussiate or potassium prussiate as one of the raw materials, or if an alkali such as sodium hydroxide is used in the hydrolysis, free glycine cannot be directly prepared as in the Strecker method. As a result, the hydantoin method involves problems of the treatment of the neutral salts and the like.

In this hydantoin method, a method for directly obtaining glycine without using an alkali such as sodium hydroxide (hereinafter referred to as "direct hydantoin method") is considered to be an economical process for preparing glycine without any environmental pollution, since by-products such as sodium sulfate and the like are not formed.

As such a direct hydantoin method, there is, for example, a method in which hydrogen cyanide, aldehyde, ammonia and carbon dioxide are heated at 100° C. or more in an aqueous solvent (U.S. Pat. No. 3,536,726).

As a decoloring technique for crude glycine obtained by the above-mentioned method, a method is known in which an aqueous crude glycine solution is usually treated with an ion exchange resin or active carbon. In addition, crystallization from methanol or washing with methanol is also effective for the decoloring.

In order to obtain free glycine by the Strecker method, a metal salt of glycine is neutralized usually with sulfuric acid or the like so as to be pH 6 to 7 or so which is convenient to crystallize glycine, followed by desalting, thereby obtaining glycine in the state of an aqueous glycine solution containing neutral salts or an aqueous glycine solution from which most of the neutral salts are separated. Afterward, decoloring is made with active carbon, an anion exchange resin or the like.

Japanese Patent Publication No. 54-1686 discloses a purification process for glycine in which a crude aqueous glycine solution having a pH of 7 or less is obtained by the Strecker method, the monochloroacetic acid method or the like is treated at 50° C. or less with a weakly basic anion exchange resin or a moderately basic anion exchange resin.

If active carbon is used for decoloring, the crude aqueous glycine solution is temporarily decolored, but when heated for concentration, it is colored again. Therefore, the prior art describes that when active carbon is used, it is necessary to repeat recrystallization for high purity and a large amount of the active carbon is required.

On the other hand, with regard to the decoloring technique of colored glycine obtained by the direct hydantoin method, U.S. Pat. No. 3,536,726 discloses that a reaction solution is directly treated with active carbon and then crystallized from methanol to prepare glycine, and Japanese Patent Laid-open No. 49-127915 discloses that a reaction solution is concentrated under reduced pressure to precipitate crystals of glycine, and the latter are then decolored with active carbon and recrystallized from water-methanol to prepare white glycine.

SUMMARY OF THE INVENTION

As described in Japanese Patent Publication No. 54-1986, when active carbon is used to decolor glycine, a large amount of the active carbon is required, and therefore this known method is neither effective nor economical.

A reaction solution obtained by the direct hydantoin method is also colored yellow or brown as in cases of other methods, and according to the investigation of examples in the above-mentioned U.S. Pat. No. 3,536,726 and Japanese Patent Laid-open No. 49-127915 by the present inventors, the treatment of this reaction solution with the active carbon is industrially quite impracticable, since the amount of the active carbon is too large. Moreover, in a process described in Japanese Patent Publication No. 54-1686, i.e., in a process in which a crude glycine solution whose pH is adjusted to 7 or less by hydrochloric acid is treated with a weakly basic anion exchange resin, a decoloring ratio was from 60 to 70%, and the life of the weakly basic anion exchange resin is short. In consequence, it is apparent that this disclosed process cannot be applied to the decoloring of glycine obtained by the direct hydantoin method.

As understood from the foregoing, the known techniques are still insufficient from industrial and economical viewpoints. In particular, an effective decoloring method for the reaction solution obtained by the direct hydantoin method has not been known at all so far.

An object of the present invention is to provide an industrially economical decoloring method for colored glycine.

The present inventors have intensively researched decoloring methods for glycine, and as a result, they have found that the decoloring power of active carbon to an aqueous glycine solution is extremely low at pH 6 to 7, and when the pH is 7 or more, colored impurities adsorbed on the active carbon are released therefrom unexpectedly, and that the active carbon used for the decoloring can be easily reactivated by treating with an aqueous alkali solution. The present invention has been completed on the basis of these knowledges. A method of the present invention for purifying glycine is characterized by comprising the steps of adjusting the pH of an aqueous glycine solution to 6 or less, and then decoloring the solution by active carbon treatment.

In case the present invention is applied to the decoloring of an aqueous glycine solution obtained by the direct hydantoin method, it is characterized by adjusting, to pH 6 or less, a glycine-containing aqueous solution prepared by removing a carbon dioxide gas and ammonia from a reaction solution obtained by reacting glycolonitrile, the carbon dioxide gas and ammonia in the presence of water, and then treating the aqueous solution with active carbon. More preferably, the present invention is characterized by separating a glycine-containing aqueous solution into glycine and a mother liquor by crystallization, recycling the mother liquor to a reactor and bringing the glycine into the state of an aqueous solution again, adjusting the pH of the solution to 6 or less, and then treating it with active carbon.

According to the method of the present invention, the decoloring of glycine can be achieved substantially completely only by the treatment with active carbon which has been heretofore considered to be industrially impracticable, and the amount of the active carbon to be used can be decreased and its reactivation is also easy.

The method of the present invention can improve the direct hydantoin method for manufacturing glycine to an industrially advantageous level.

DETAILED DESCRIPTION OF THE INVENTION

In the present invention, an aqueous crude glycine solution obtained by any method can be applicable. Furthermore, if glycine is present in the state of a solution in a manufacturing process, the present invention can be applied thereto. The concentration of glycine in the solution is from 2 to 45% by weight, preferably from 5 to 35% by weight at the time of a treatment with active carbon. When the glycine concentration is less than 5% by weight, the concentration cost of the decolored aqueous glycine solution increases. Conversely, when it is more than 35% by weight, glycine is precipitated, and thus it is necessary to maintain an active carbon column at 80° C. or more, so that coloring is inconveniently caused and, when an ion exchange resin is used to adjust the pH of the aqueous solution to be treated, the deterioration of this resin is accelerated unpreferably.

In the aqueous glycine solution to be decolored, the concentration of inorganic salts such as sodium chloride, sodium sulfate, ammonium chloride and ammonium carbonate is preferably 10% by weight or less, most preferably substantially 0%. Therefore, it is preferred that these salts are separated prior to the treatment with the active carbon.

The adjustment of the aqueous glycine solution to pH 6 or less can be achieved by adding a mineral acid such as sulfuric acid, phosphoric acid or hydrochloric acid, or an organic acid such as formic acid, acetic acid or oxalic acid, or alternatively by treating the aqueous solution with an acidic cation exchange resin.

The acidic cation exchange resin which is used in the method of the present invention is commercially available. Examples of this kind of ion exchange resin include, in terms of trade names, Amberlite IR-116, IR-252 and IRC-84 (Japan Organo Co., Ltd.), Diaion SK102, Sk110, PK212, WK10 and WK20 (Mitsubishi Chemical Industries, Ltd.), and Rebatit S100, SP112 and CNP80 (Mitsui Toatsu Fine Co., Ltd.). The cation exchange resin itself has no decoloring ability but is preferable as a means for adjusting the pH of the aqueous glycine solution which is important in the present invention. Above all, when a strongly acidic cation exchange resin is used, the pH can be adjusted to a low level of from 4 to 5, and when adjusted to such a low level, the decoloring power of the active carbon in the following step can be heightened and the life of the active carbon can be prolonged preferably. With regard to the ion type of the acidic cation exchange resin, a salt type is acceptable, but an H type is preferably used.

The lower the pH of the pH-adjusted solution is, the better, but when the pH is less than 2, expensive materials are required for devices, and when it is from 2.5 to 3.5, the solubility of glycine in water increases, which has an adverse influence on the subsequent crystallization step. On the other hand, when the pH is in excess of 6, the decoloring power of the active carbon is poor, and when it is 7 or more, the colored material adsorbed on the active carbon is released therefrom. Therefore, the pH of the aqueous glycine solution is preferably in the range of from 3.5 to 6, more preferably from 4 to 5.5, and most preferably from 4.5 to 5.3.

The active carbon which can be used in the present invention may be what is made of a plant such as coconut shells or a mineral such as a coal or a pitch. Exemplary trade names of the active carbons made of the coconut shells include Shirasagi C (Takeda Chemical Industries, Ltd.) and Tsurumicol HC-30 (Tsurumi Co., Ltd.), and exemplary trade names of the active carbons made of the coal include CPG and CAL (Toyo Karugon Co., Ltd.) and A-BAG (Kureha Chemical Industry Co., Ltd.). Above all, the particularly preferable active carbon is CPG which has been subjected to an acidic treatment so that trace components of the active carbon may not be dissolved out even when an acidic solution is passed therethrough.

In the present invention, the pH adjustment by the acidic cation exchange resin or the decoloring treatment by the active carbon can be effectively accomplished by passing the solution through towers packed therewith, and this manner is usually carried out. In passing the solution, a ratio of a packing length/diameter of each of the acidic cation exchange resin and the active carbon is in the range of from 2 to 20, and a passage velocity is in the range of from 0.1 to 20 in terms of SV (solution space velocity). No restriction is put on a temperature at the pH adjustment and a temperature at the declaring by the active carbon, but preferably, the temperature during pH adjustment by the acidic cation exchange resin is from 20 to 80° C., and the temperature during decoloring by the active carbon is from 20 to 100° C.

If necessary, after the active carbon treatment or before the acidic treatment, an anion exchange,,: resin can be used to remove anions and extremely slightly colored substances which cannot be removed by the active carbon alone, whereby it can be expected to heighten the purity of glycine.

The present inventors have found that the active carbon for the decoloring which has been used in the present invention can be easily recovered by the use of a prevalent aqueous alkaline solution such as sodium hydroxide. In addition, it has also been found that the above-mentioned reactivation efficiency can be further improved by the use of an aqueous alkaline solution containing a mineral acid salt such as sodium chloride. The reactivation of the active carbon can be preferably achieved by passing an aqueous alkaline solution (0.1 to 10 equivalents) such as sodium hydroxide in an amount 2 to 30 times as much as that of the active carbon to be reactivated at SV of 0.05 to 20 (1/H) to release impurities adsorbed on the active carbon therefrom, and then washing the active carbon with water in an amount of 2 to 50 times as much as that of the active carbon to be reactivated. In this washing step, it is more preferable to use an aqueous alkaline solution containing a mineral acid salt such as sodium chloride or sodium sulfate. The content of the above-mentioned salt in the aqueous alkaline solution is preferably in the range of from 1 to 20% by weight, more preferably from 5 to 10% by weight. As a result, the removal operation of the active carbon for the reactivation is unnecessary which is carried out in most of other manufacturing methods using the active carbon, and the amount of the active carbon to be freshly packed can be decreased. The preferable recovery temperature is in the range of from 20 to 100° C.

The method of the present invention will be described in detail in reference to an example of the pH adjustment of a reaction solution obtained by the direct hydantoin method.

Glycolonitrile which is used in the direct hydantoin method can be prepared from hydrocyanic acid and formalin, which is the most general and economical manufacturing process. As the formalin source, a solution obtained by dissolving paraformaldehyde in water can also be used. The production reaction of glycolonitrile is quick, and for example, glycolonitrile can be easily produced by blowing a hydrocyanic acid gas into an aqueous formalin solution, or by mixing a hydrocyanic acid solution with an aqueous formalin solution. The reaction temperature is from 0 to 80° C., and the reaction time is from 2 minutes to 5 hours. Furthermore, glycolonitrile containing a stabilizer such as sulfuric acid or phosphoric acid can also be used.

In the process of the present invention, ammonia and the carbon dioxide gas themselves may be directly used, but known compounds in the art which can produce these compounds (ammonia and he carbon dioxide gas) under reaction conditions, for example, ammonium carbonate or ammonium bicarbonate may be used. In addition, when these compounds are used in the form of a mixture, preferable results can be similarly obtained.

The amount of ammonia to be used is in the range of from 1 to 12 mols, preferably from 4 to 9 mols based on one mol of glycolonitrile. When the amount of ammonia is less than 1 mol, the reaction is slow, and when it is more than 12 mols, the amount of by-products increases and reaction pressure also increases unpreferably, though the reaction rate is accelerated. In addition, the amount of the carbon dioxide gas to be used is from ½ to 3 mols based on one mol of ammonia. It is preferred that the amount of the carbon dioxide gas is in this range, since the reaction rate is quick and the reaction pressure is low.

In the method of the present invention, the amount of water to be used is in the range of from 3 to 15 mols based on one mol of ammonia. When the amount of water is less than 3 mols, the selectivity of glycine is low, and in order to obtain glycine having a certain purity, the crystallization ratio of glycine extremely deteriorates. Conversely, when water is used in an amount in excess of 15 mols, the selectivity of glycine increases, but the concentration of glycine in the reaction solution decreases, so that the cost of the concentration for the crystallization increases and a large reactor is uneconomically required.

In the present invention, when the reaction temperature is low, the yield of glycine is high but the reaction rate is slow. However, when the reaction temperature is high, the reaction solution is noticeably colored. Therefore, the reaction temperature is from 100 to 200° C., preferably from 140 to 180° C., more preferably from 150 to 170° C. Furthermore, the reaction time is usually from 30 minutes to 20 hours, preferably from 1 to 10 hours.

No particular restriction is put on the reaction pressure, and the reaction can be carried out under a pressure higher than the pressure generated during the reaction and it can also be carried out while ammonia, the carbon dioxide gas, a water vapor or the like generated during the reaction are suitably drawn off.

After completion of the reaction under these conditions, in this reaction solution containing glycine, glycolonitrile is not substantially present but there are contained hydantoic acid, glycyl glycine, hydantoic amide, triglycine, hydantoin, 2,5-diketopiperazine and the like.

The above-mentioned reaction solution is concentrated and then subjected to the undermentioned crystallization to separate glycine therefrom. In particular, the reaction solution is flushed and/or heated at 50°-200° C. under about 10 mmHg-30 kg/cm² to vaporize water, whereby the reaction solution is concentrated. At this time, usually, ammonia and the carbon dioxide gas are also vaporized and separated from the reaction solution. Alternatively, an inert gas such as air and nitrogen can be blown into the reaction solution at 50°-200° C. under about 10 mmHg-30 kg/cm² to strip the carbon dioxide gas and ammonia therefrom, whereby they can be separated from the reaction solution. The concentration of the reaction solution is carried out for a period of from about 10 seconds to 20 hours, preferably from about 1 minute to 10 hours. The important point of this process is that the separation of the carbon dioxide gas and ammonia from the reaction solution is achieved sufficiently. When the separation of the carbon dioxide gas and ammonia is insufficient, ammonium carbonate produced therefrom is precipitated and adheres to glycine crystals in the step in which the concentrate is crystallized to separate glycine. As a result, the amount of the colored mother liquor which adheres to the glycine crystals is larger than in the case of the high-purity glycine crystals, and a large amount of a rinsing liquor is required. In addition, when a mineral acid is used to adjust the pH, an ammonium salt of the mineral acid is formed, and when an acidic cation exchange resin is used for the acidic treatment, the life of this resin is shortened unpreferably. Therefore, the concentration of the remaining carbon dioxide gas and ammonia in the concentrate is preferably 10% by weight or less in terms of ammonium carbonate.

The above-mentioned concentrate may be directly subjected to the pH adjustment and the active carbon treatment, but preferably, as described below, glycine is separated therefrom and then dissolved in water, and the resultant aqueous glycine solution is used.

In this case, the concentrate is cooled to, for example, about 0 to 80° C., to precipitate the glycine crystals. This precipitation of glycine from the concentrate is carried out by a known method, and for example, a crystallization method such as a cooling crystallization method, a vaporization crystallization method or a vacuum crystallization method can be industrially preferably used. Alternatively, a crude solvent such as methanol may be added to the concentrate, followed by crystallization. A slurry obtained by the above-mentioned crystallization is then separated into glycine crystals and a mother liquor by the use of a prevalent separator, and the mother liquor is returned to a reactor. The recycling of the mother liquor permits effective reutilization of ammonia carbonate in the mother liquor and remarkably improves the yield of glycine. At this time, a crystallization ratio is preferably 40% by weight or more. When the crystallization ratio is less than 40% by weight, a larger reactor is required, and the cost of concentration associated with the crystallization increases uneconomically. However, even when the crystallization ratio is 40% by weight or more, glycine having a purity of 95% by weight or more can be obtained.

When the aqueous solution of the glycine crystals is prepared, its pH can be controlled to some extent by adjusting the concentration ratio of the reaction solution, but in the case of a usual concentrating operation, the pH is inconveniently in the range of from 8 to 9.

Prior to the separation of glycine by means of a centrifugal separator, the glycine crystals are preferably washed with water or an aqueous glycine solution in an amount of from 15 to 35% by weight based on the weight of glycine crystals to heighten the purity of glycine and to remove ammonia adhering to the glycine crystals therefrom. Nevertheless, the pH of a solution prepared by dissolving the glycine crystals in water is still from about 6.5 to 7.5.

This aqueous glycine solution cannot be directly treated with active carbon, because perfect decoloring cannot be achieved and the life of the active carbon is shortened. Hence, the aqueous glycine solution is adjusted to pH 6 or less by the above-mentioned procedure. In the case of the procedure of separating glycine from the above-mentioned concentrate by crystallization, recycling the resultant mother liquor to the reactor, and then dissolving the precipitated glycine in water to decolor the same, it is particularly preferred to use an acidic cation exchange resin for the pH adjustment, because mineral acids or organic acids are not accumulated and the glycine crystals are not contaminated therewith. The aqueous glycine solution having a pH of 6 or less can be decolored substantially completely by the subsequent active carbon treatment, and the reoccurrence of coloring is scarcely perceived and the life of the active carbon can be remarkably prolonged.

Now, the present invention will be described in detail in reference to examples.

EXAMPLE 1

2220 g of an aqueous solution containing 115 g (2.01 mols) of glycolonitrile, 206 g (12.1 mols) of ammonia and 267 g (6.1 mols) of a carbon dioxide gas per hour was fed to a pipe type reactor having an internal volume of 10 liters. Reaction was then carried out at a reaction temperature of 150° C. under a reaction pressure of 32 kg/cm$^2$-G.

At this time, the composition of the raw materials was $H_2O/NH_3/CO_2$/glycolonitrile=45/6/3/1 in terms of molar ratio, and an average residence time corresponded to 5 hours. When a steady state was reached, a reaction solution was continuously concentrated at 100° C. under atmospheric pressure to remove 1830 g of water, ammonia and a carbon dioxide gas in total, followed by crystallization at 5° C. Rinsing was then carried out by the use of 16 g of pure water at 5° C. per hour to separate 0.89 mol (purity 98.2% by weight) of glycine. The remaining mother liquor was analyzed, and as a result, 0.97 mol of hydantoic acid, glycylglycine, hydantoic amide, 2,5-diketopiperazine, hydantoin, triglycine and glycine in total in terms of glycolonitrile was detected. The mother liquor for an initial feed was prepared in this way.

Next, this mother liquor, a 50% by weight aqueous glycolonitrile solution and an aqueous ammonium carbonate solution were fed to the reactor so that the composition of these components might be identical with the feed composition in terms of glycolonitrile. That is, 2220 g of an aqueous solution containing this mother liquor, 59 g (1.04 mols) of glycolonitrile and 6.1 mols of ammonium carbonate per hour were fed to the reactor. The resulting reaction solution was continuously concentrated at a temperature of 100° C. by the use of the concentrator to remove 1916 g of water, ammonia and the carbon dioxide gas in total therefrom. Crystallization was then made at 5° C., so that 68 g of glycine (purity 98.6%) per hour was separated. This amount corresponded to a glycine isolated yield of 86%. In this concentration step, most of ammonia and the carbon dioxide gas were removed therefrom.

The thus obtained glycine crystals (purity 98.6%) were dissolved in water at 70° C. to prepare a 20% by weight aqueous glycine solution (pH 7.3) for decoloring. The chromaticity of this aqueous glycine solution was APHA 162.

Tube type towers having diameters of 3.5 cm and 2.5 cm were packed with 300 ml of an H type weakly acidic cation exchange resin (Rebatit CNP80) and 100 ml of active carbon (CPG), respectively, which were subjected to a pretreatment in a usual way, and 50 kg of the aqueous glycine solution was passed through the tower at 25° C. at a rate of 200 ml/hour. As a result, the aqueous solution had a pH of 5.5 and a chromaticity of APHA 148 at the outlet of the acidic cation exchange resin tower, and the chromaticity at the outlet of the active carbon tower was APHA 2.3. At this time, the recovery of glycine was 99.8%. The results are set forth in Table 1. The resultant decolored solution was concentrated, but coloring scarcely increased. 1 g of the glycine crystals (purity 99.3% by weight) obtained by cooling was dissolved in 10 g of water, and absorbance (10 mm cell) was then inspected. As a result, values of the absorbance at both the wavelengths of 370 nm and 430 nm were the same and from 0.000 to 0.005, which corresponded to APHA 0 to 3. In addition, commercially available glycine was measured in the same manner, and as a result, its chromaticity was in the range of APHA 3 to 6.

The above-mentioned aqueous glycine solution obtained by the active carbon treatment was further treated with a strongly basic anion exchange resin (Rebatit MP500), followed by concentration and cooling. The chromaticity of the resultant glycine crystals was from APHA 0 to APHA 2, and glycine having a higher purity was obtained.

5 liters of 1N sodium hydroxide were passed through the used active carbon at 100 ml/hour, and the active carbon was then washed with pure water until pH 8 was reached and then reused. Even when 10 kg of the same aqueous glycine solution for decoloring was passed through the thus reactivated active carbon, the chromaticity of the solution at the outlet of the active carbon tower was APHA 0.9.

EXAMPLE 2

A decoloring test was carried out following the same procedure as in Example 1 except that the weakly acidic cation exchange resin was replaced with a strongly acidic cation exchange resin (Rebatit SP112) and that the active carbon of Shirasagi C was used. As a result, the glycine solution has a pH of 4.5 and a chromaticity of APHA 139 at the outlet of an acidic cation exchange resin tower, and when 50 kg of the solution was passed through the active carbon, the chromaticity at the outlet of an active carbon tower was APHA 1.8 or less. The recovery of glycine was 99.2%. The results are set forth in Table 1.

EXAMPLE 3

An active carbon treatment was carried out following the same procedure as in Example 1 except that any weakly acidic cation exchange resin was not used and that the pH of an aqueous glycine solution was adjusted to 5.0 by phosphoric acid. As a result, when 10 kg of the glycine solution was passed through active carbon, its chromaticity at the outlet of an active carbon tower was APHA 0.6. At this time, the recovery of glycine was 99.4%.

COMPARATIVE EXAMPLE 1

A decoloring test was carried out following the same procedure as in Example 1 except that the 20% by weight aqueous glycine solution (pH 7.3, chromaticity APHA 162) obtained in Example 1 was directly treated with active carbon (CPG) without pretreatment with an acidic cation exchange resin. When 10 kg of the aqueous glycine solution was passed through the active carbon, its chromaticity at the outlet of an active carbon tower was APHA 14. Glycine crystals obtained by crystallizing the decolored aqueous glycine solution had a chromaticity of APHA 6 to APHA 10. In addition, when 50 kg of the solution in total was passed therethrough, the chromaticity at the outlet of the active carbon tower further increased. The results are set forth in Table 1.

COMPARATIVE EXAMPLE 2

A decoloring test was carried out following the same procedure as in Example 1 except that glycine crystals were collected without rinsing and dissolved in water at 60° C. to prepare a 20% by weight aqueous glycine solution (pH 8.1, APHA 193) for decoloring and that the glycine solution was directly treated with active carbon (CPG) without pretreatment with the acidic cation exchange resin. When 10 kg of the aqueous glycine solution was passed through the active carbon, its chromaticity at the outlet of an active carbon tower was APHA 20. The results are set forth in Table 1.

TABLE 1

| Amount of Solution (kg) | 2 | 5 | 10 | 15 | 20 | 30 | 40 | 50 |
|---|---|---|---|---|---|---|---|---|
| Example 1 (APHA) | 0 | 0.3 | 0.6 | 1.7 | 1.5 | 2.1 | 1.9 | 2.3 |
| Example 2 (APHA) | 0 | 0.2 | 0.5 | 0.9 | 1.2 | 1.5 | 1.5 | 1.8 |
| Comp. Ex. 1 (APHA) | 0.5 | 2.0 | 14 | 16 | 19 | 24 | 26 | 32 |
| Comp. Ex. 2 (APHA) | 0.5 | 15 | 20 | 22 | 28 | 31 | 35 | 46 |

EXAMPLE 4

2220 g of an aqueous solution containing 115 g (2.01 mols) of glycolonitrile, 206 g (12.1 mols) of ammonia and 267 g (6.1 mols) of a carbon dioxide gas per hour was fed to a pipe type reactor having an internal volume of 10 liters. Reaction was then carried out at a reaction temperature of 150° C. under a reaction pressure of 32 kg/cm$^2$-G.

At this time, the composition of the raw materials was $H_2O/NH_3/CO_2$/glycolonitrile=45/6/3/1 (molar ratio), and an average residence time corresponded to 5 hours. When a steady state was reached, a reaction solution (APHA 720, glycine concentration 5% by weight) was treated in the same manner as in Example 1. Tube type towers having diameters of 3.5 cm and 2.5 cm were packed with 1000 ml of an H type strongly acidic cation exchange resin Amberlite 200CT) and 100 ml of active carbon (CPG), respectively, which were subjected to a pretreatment in a usual way, and when 10 kg of the reaction solution containing glycine was passed through the towers at 25° C. at a rate of 200 ml/hour, and the chromaticity of the solution at the outlet of an active carbon tower was APHA 3.6. Furthermore, the decolored solution was concentrated and then crystallized to obtain glycine crystals (purity 98.6% by weight), and 1 g of the thus obtained glycine crystals was dissolved in 10 g of water. The resultant aqueous glycine solution had a chromaticity of APHA 3, and so its quality was satisfactory.

EXAMPLE 5

A decoloring test was carried out following the same procedure as in Example 4 except that the acidic cation exchange resin was not used and pH was adjusted to 4.5 by phosphoric acid. At the time when 10 kg of a reaction solution containing glycine was passed through active carbon, a decolored solution was concentrated and crystallized to obtain glycine crystals, and the chromaticity of the thus obtained glycine crystals was APHA 3, and the quality thereof was satisfactory.

COMPARATIVE EXAMPLE 3

A decoloring test was carried out following the same procedure as in Example 4 except that the pH of a reaction solution was not adjusted by the acidic cation exchange resin. When 5 kg of a reaction solution was passed through active carbon, the chromaticity of the solution at the outlet of an active carbon tower was already APHA 52. Methanol was added to the solution to precipitate glycine. The chromaticity of the glycine crystals was APHA 12, and satisfactory quality was not obtained.

COMPARATIVE EXAMPLE 4

A decoloring test was carried out following the same procedure as in Example 1 except that the acidic cation exchange resin and active carbon were not used and that a weakly basic anion exchange resin (Amberlite IRA-93, 300 ml) was used. When 10 kg of an aqueous glycine solution was passed through the resin, the chromaticity of the solution at the outlet of the anion exchange resin tower was APHA 23. The thus decolored solution was concentrated and crystallized to obtain glycine crystals, and 1 g of the glycine crystals was dissolved in 10 g of water. The chromaticity of the resultant aqueous glycine solution was APHA 9, and satisfactory quality was not obtained.

What is claimed is:

1. A method for preparing purified glycine crystals which comprises the steps of reacting glycolonitrile, carbon dioxide gas and ammonia in the presence of water to obtain an aqueous reaction solution containing glycine, removing most of any remaining carbon dioxide gas and ammonia from the reaction solution, adjusting the pH of the remaining alkaline aqueous glycine solution to 3.5–6 with an acidic cation exchange resin, decoloring said aqueous glycine solution by contacting the solution with active carbon, and evaporating water from the solution to crystallize pure glycine crystals.

2. The method for preparing purified glycine crystals according to claim 1 wherein said active carbon is reactivated with an aqueous alkaline solution after decoloring said aqueous glycine solution.

3. A method for preparing purified glycine crystals which comprises the steps of reacting glycolonitrile, carbon dioxide gas, and ammonia in the presence of water to obtain an aqueous reaction solution containing glycine, removing most of any remaining carbon dioxide gas and ammonia from the reaction solution, crystallizing glycine from said reaction solution, adjusting the pH of the aqueous solution of said crystallized glycine to 3.5–6 with an acidic cation exchange resin, and then decoloring said aqueous glycine solution by contacting the solution with active carbon and evaporating water from the solution to crystallize pure glycine crystals.

4. The method for preparing purified glycine crystals according to claim 3 wherein said active carbon is reactivated with an aqueous alkaline solution after decoloring said aqueous glycine solution.

* * * * *